United States Patent [19]

Outttrup et al.

[11] Patent Number: 5,358,865
[45] Date of Patent: Oct. 25, 1994

[54] ALKALINE PROTEASE FROM *BACILLUS J 20*

[75] Inventors: Helle Outtrup, Ballerup; Claus Dambmann, Soeborg; Dorrit A. Aaslyng, Roskilde, all of Denmark

[73] Assignee: Novo Nordisk A/S, Bagsvaerd, Denmark

[21] Appl. No.: 975,553

[22] PCT Filed: Oct. 11, 1991

[86] PCT No.: PCT/DK91/00309
§ 371 Date: Feb. 22, 1993
§ 102(e) Date: Feb. 22, 1993

[87] PCT Pub. No.: WO92/07067
PCT Pub. Date: Apr. 30, 1992

[30] Foreign Application Priority Data

Oct. 12, 1990 [DK] Denmark ............... 2462/90

[51] Int. Cl.⁵ .............. C12N 9/52; C12N 9/54; C11D 3/386
[52] U.S. Cl. ............... 435/221; 435/220; 252/174.12; 252/DIG. 12
[58] Field of Search ............... 435/220, 221; 252/174.12, DIG. 12

[56] References Cited

U.S. PATENT DOCUMENTS

| | | | |
|---|---|---|---|
| 3,622,458 | 11/1971 | Murao | 435/222 |
| 3,871,963 | 3/1975 | Tobe et al. | 435/221 |
| 3,905,869 | 9/1975 | Hidaka et al. | 435/221 |
| 4,052,262 | 10/1977 | Horikoshi et al. | 435/221 |
| 4,364,926 | 12/1982 | Yokogawa et al. | 424/50 |
| 4,480,037 | 10/1984 | Ichishima et al. | 435/221 |
| 4,511,490 | 4/1985 | Stanislowski et al. | 252/174.12 |
| 4,764,470 | 8/1988 | Durham et al. | 435/221 |
| 4,771,003 | 9/1988 | Stellwag et al. | 435/221 |
| 4,797,362 | 1/1989 | Takeuchi et al. | 435/221 |
| 5,143,840 | 9/1992 | Rettenmaier et al. | 435/221 |

OTHER PUBLICATIONS

Tsuru et al, (1967) *Agr. Biol. Chem.*, 31(3), 330–335.
Munnelly et al., *Int. J. Peptide Protein Res.*, vol. 8, pp. 141–153 (1976).
Takii et al., *Appl. Micro. Bio.*, vol. 34, pp. 57–62 (1990).

*Primary Examiner*—Douglas W. Robinson
*Assistant Examiner*—Jon P. Weber
*Attorney, Agent, or Firm*—Steve T. Zelson; Karen A. Lowney

[57] ABSTRACT

An alkaline protease isolated from a strain of Bacillus sp. J 20 is disclosed. The protease has a mass of about 29 kD, a pI of about 8.8, a pH optimum above 10, and a temperature optimum of about 45° to 65° C. The use of the protease as a detergent enzyme, as well as detergent compositions and detergent additives comprising the protease is also disclosed.

9 Claims, 2 Drawing Sheets

5,358,865

ALKALINE PROTEASE FROM *BACILLUS J 20*

TECHNICAL FIELD

This invention is in the field of detergent proteases derived from strains of alkalophilic Bacillus sp. More specifically, the invention is directed towards a novel alkaline protease derived from a strain of Bacillus sp. J 20. Moreover, the invention is directed towards a process for the preparation of the protease, the use of the protease as detergent enzyme, as well as detergent compositions and detergent additives comprising the protease of the invention.

BACKGROUND ART

Detergent enzymes have been marketed for more than 20 years and are now well established as normal detergent ingredients in both powder and liquid detergents all over the world. With the trend toward lower temperature washing, detergent enzyme consumption has increased during late years. Enzymes used in washing formulations comprise proteases, lipases, amylases, cellulases, as well as other enzymes, or mixtures hereof. Commercially most important are proteases.

Detergent proteases have been developed by isolation of proteases found in nature followed by testing in detergent formulations. Most detergent proteases are obtained from members of the genus Bacillus. Currently new types of proteases enter the market, offering the possibility of giving a better cost/performance ratio at various specified conditions.

Examples of commercial protease products are ALCALASE ™, ESPERASE ™ and SAVINASE ™, all supplied by Novo Nordisk A/S, Denmark. These and similar enzyme products from other commercial sources are active in detergent solutions, i.e. at pH values in the range from 8 to 11 and in the presence of sequestering agents, surfactants and bleaching agents such as sodium borate. The ALCALASE ™ protease is produced by strains of the species *Bacillus licheniformis*. The ESPERASE ™ and SAVINASE ™ proteases are obtained by cultivation of strains of alkalophilic Bacilli.

SUMMARY OF THE INVENTION

According to the present invention there are provided novel detergent proteases with excellent washability.

In its first aspect, the invention provides a protease having an apparent molecular weight of 29 kD; pI around 8.8; pH optimum in the range of from pH 10 to 12 (at 25° C.); temperature optimum in the range of from 45° to 65° C. (at pH 9.5).

In another aspect, the invention provides a protease having an apparent molecular weight of 29 kD; pI around 8.8; pH optimum in the range of from pH 10 to 12 (at 25° C.); temperature optimum in the range of from 45° to 65° C. (at pH 9.5); and immunochemical properties identical or partially identical to those of a protease derived from Bacillus sp. J 20, NCIMB No. 40262. In a more specific aspect, the protease is obtainable from a strain of Bacillus sp. J 20. In a yet more specific aspect, the protease is obtainable from Bacillus sp. J 20, NCIMB No. 40262, or a mutant or a variant thereof.

In a third aspect, the invention provides an isolated biologically pure culture of a strain of Bacillus sp. J 20. In a more specific aspect, a strain of Bacillus sp. J 20, NCIMB No. 40262, or a mutant or a variant thereof, is provided.

In a fourth aspect, the invention provides a process for the preparation of the protease, which process comprises cultivation of a protease producing strain of Bacillus sp. J 20 in a suitable nutrient medium, containing carbon and nitrogen sources and inorganic salts, followed by recovery of the desired enzyme. In a more specific aspect, Bacillus sp. J 20, NCIMB No. 40262, or a mutant or a variant thereof, is cultivated.

In a fifth aspect, the use of the enzyme as detergent enzyme is claimed. In a more specific aspect, the invention provides a detergent composition comprising the protease. In another specific aspect, the invention provides detergent additives comprising the protease.

BRIEF DESCRIPTION OF DRAWINGS

The present invention is further illustrated by reference to the accompanying drawings, in which.

DETAILED DISCLOSURE OF THE INVENTION

The Microrganism

Figure 1:
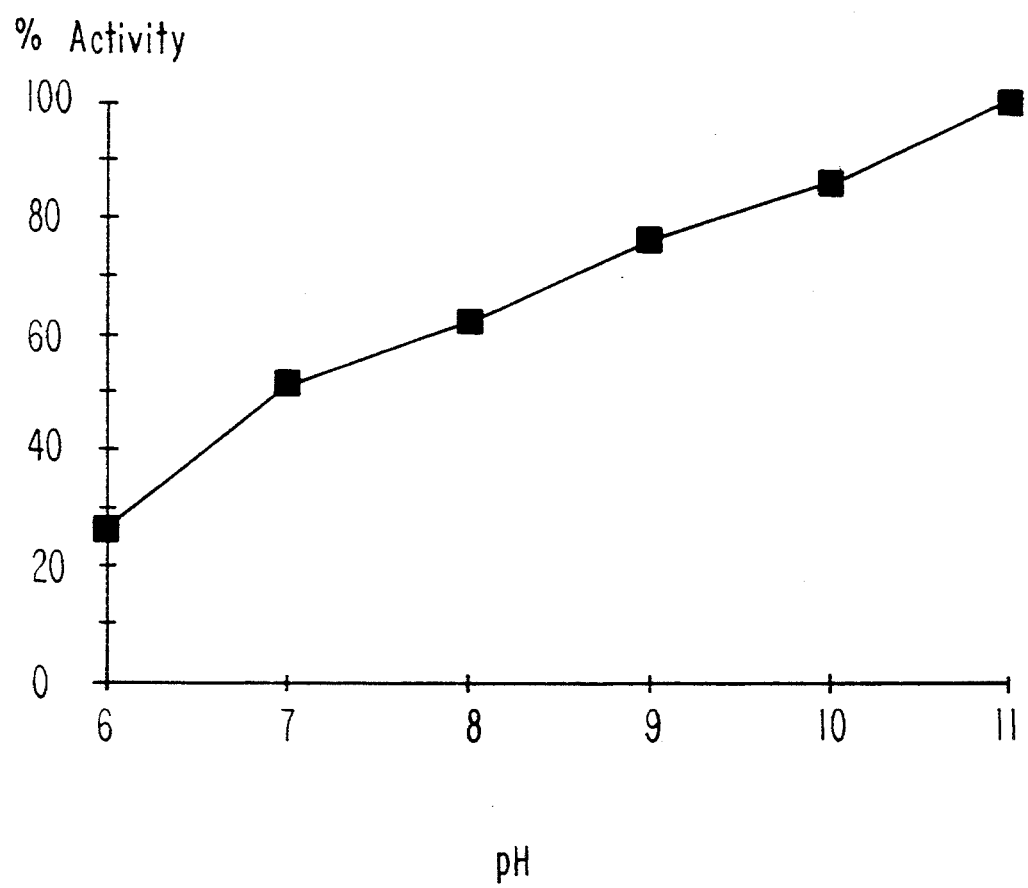
FIG. 1 shows the relation (% relative activity) between temperature and proteolytic activity of an enzyme according to the invention (with casein as substrate and at pH 9.5) in the presence and absence of STTP (■ J20; □ J20+0.1% STPP)

The novel microorganisms of the invention, able to produce an enzyme of the invention, were isolated essentially by the method for selection of alkalophilic Bacilli described in British Patent No. 1,243,784. One such culture, Bacillus sp. J 20, has been deposited on 27 February 1990 according to the Budapest Treaty at NCIMB Ltd., 23 St. Machar Drive, Aberdeen AB2 1RY, Scotland, UK, with Accession No. NCIMB 40262.

The microorganism of this invention is an aerobic, spore forming bacterium belonging to the genus Bacillus. Morphologically it can be described as motile rods with a diameter of 0.6–0.8 micron, and a length of 2–3 micron. The spores are round to ellipsoid, not swelling the sporangium, central to subterminal. Optimal temperature for growth is within 35°–40° C., and optimal pH for growth is within 8.5–10, no growth below pH 8. The microorganism forms yellow colonies on nutrient agar slants, and no diffusion of pigment into the agar is observed.

The microorganism of the invention can be further characterized by the test results cited in Table 1.

TABLE 1

| TEST | DSM 485 | DSM 497[2] | J 20 |
|---|---|---|---|
| Nutrient agar (Difco) pH 9[1] | + | + | + |
| Nutrient agar (Difco) pH 7[1] | w | – | w |
| Nutrient agar (Difco) pH 11[1] | + | – | – |
| B. Subtilin minimal medium (Spizizen) pH 7[1] | w | – | w |
| Growth at 50° C.[1] | – | + | – |
| Growth in NaCl: | | | |
| 2% | – | + | + |
| 5% | – | + | + |
| 7% | – | + | + |
| 10% | – | + | (+)[3] |
| Hydrolysis of: | | | |
| Starch | + | + | + |

TABLE 1-continued

| TEST | DSM 485 | DSM 497[2] | J 20 |
|---|---|---|---|
| Casein | + | + | + |
| Gelatin | + | + | + |
| CMC | − | − | − |
| Acid from: | | | |
| Glucose | + | W | − |
| Mannitol | − | + | − |
| Sorbitol | − | − | − |
| Xylose | − | − | − |
| Reduction of: | | | |
| Nitrate | − | − | + |
| Anaerobic growth | − | − | − |
| Voges Proskauer reaction | − | − | − |

DSM 485: B. alkalophilus
DSM 497: B. alkalophilus subsp. halodurans
J 20: B. sp. J 20, NCIMB No. 40262
W = Weak
[1]Recorded after incubation for 2 days. All other incubations for 7 days.
[2]Data from literature
[3]Positive after incubation for 14 days; negative after 7 days.

Cultivation of the Microorganism

The microorganism of the invention can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as cereal grain; malt; rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes involving the cultivation of bacteria. Illustrative examples are soybean meal; cotton seed meal; peanut meal; casein; corn; corn steep liquor; yeast extract; urea and albumin. In addition, the nutrient medium should also contain usual trace substances.

Since the novel Bacillus species of this invention are alkalophilic, and unable to grow at pH below 8, the cultivation is preferably conducted at alkaline pH values, which can be obtained by addition of suitable buffers such as sodium carbonate or mixtures of sodium carbonate and sodium bicarbonate, after sterilization of the growth medium. For cultivation in tank fermenters it is necessary to use artificial aeration. The rate of aeration is similar to that used in conventional tank fermentation.

After fermentation, liquid enzyme concentrates may be produced by removal of coarse material from the broth or, if desired, concentration of the broth by evaporation at low temperature or by reverse osmosis. Finally, preservatives may be added to the concentrate.

Solid enzyme preparations may be prepared from the purified and/or concentrated broth by precipitation with salts, such as $Na_2SO_4$ or water-miscible solvents, such as ethanol or acetone; removal of the water in the broth by suitable drying methods such as spray-drying may also be employed.

The proteolytic activity of the protease preparation so obtained is usually in the range of from 1 to 50 CPU/g.

Assay for Proteolytic Activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5. A folder AF 228, describing the analytical method, is available upon request to Novo Nordisk A/S, Denmark, which folder is hereby included by reference.

The Enzyme

The enzyme of the invention is a novel detergent protease. It is an alkaline protease, obtainable by cultivation of a microorganism of the invention, preferably Bacillus sp. J 20, NCIMB No. 40262, or a mutant or a variant thereof, in a suitable nutrient medium, containing carbon and nitrogen sources and inorganic salts. The enzyme can also be obtained by recombinant DNA-technology.

The protease of the invention can be described by the following characteristics.

Physical-Chemical Properties

A molecular weight of 29 kD, determined by SDS-PAGE. A pI of 8.8 determined by isoelectric focusing on LKB Ampholine ™ PAG plates. The protease activity is inhibited by PMSF, α-1-antitrypsin and Turkey-egg-white proteinase inhibitor. EDTA and soybean-protein inhibitor do not influence the protease activity. The protease cleaves human insulin at the C-terminal side of hydrophobic amino acids. Specifically, human insulin is cleaved between the following amino acids: in the A-chain $Leu_{13}$-$Tyr_{14}$; and in the B-chain $Leu_{11}$-$Val_{12}$, $Leu_{15}$-$Tyr_{16}$ and $Cys_{19}$-$Gly_{20}$ (Cys as a disulfide).

The temperature-activity relationship was determined with casein as substrate. The assay for proteolytic activity described previously was used with the modification that the incubation temperature was varied in the interval of from 15° to 60° C. The enzyme reaction was conducted in the presence and absence of 0.1% sodium tripolyphosphate (STPP). The results are presented in FIG. 1. The enzyme possesses proteolytic activity from temperatures below 15° C. to above 70° C., and a temperature optimum (in the absence of STPP) in the range of from 45° to 65° C.; more specifically 55° to 65° C.; around 60° C.

Figure 2:
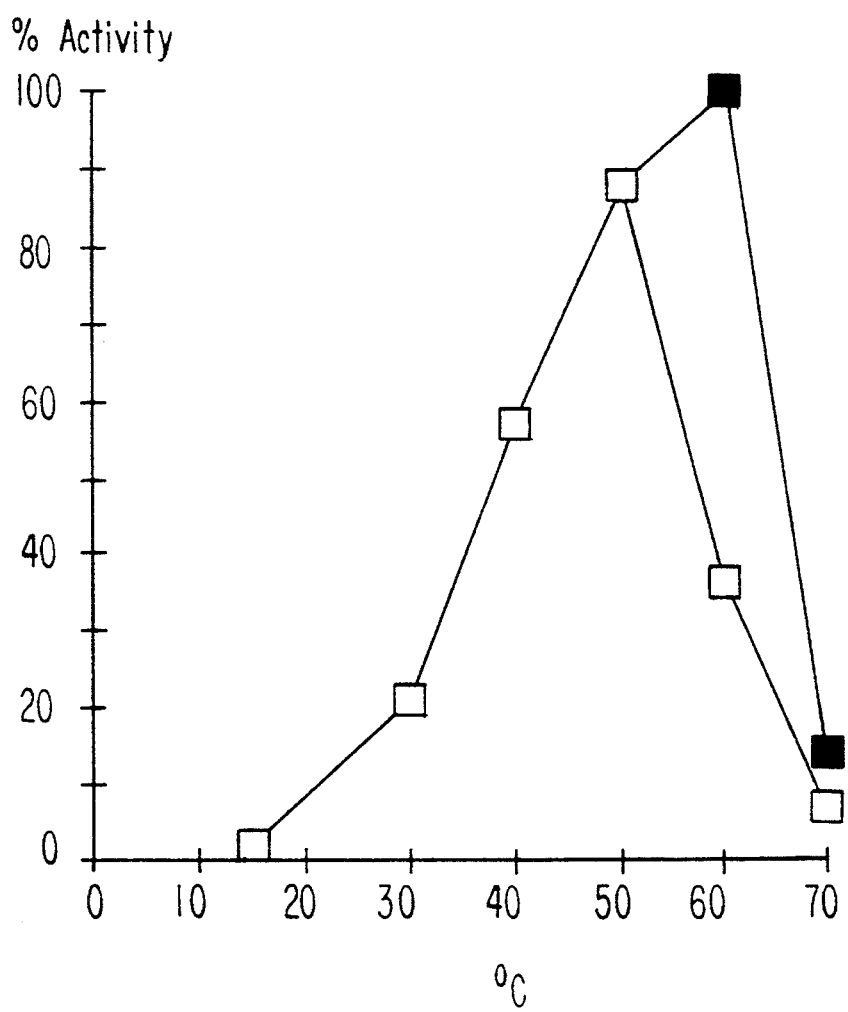
FIG. 2 shows the relation (% relative activity) between pH and the proteolytic activity of an enzyme according to the invention (with casein as substrate and at 25° C.).

The dependence of activity on pH was determined by the same procedure, using buffers adjusted to predetermined pH values in the pH range of from 7 to 11. The result is presented in FIG. 2. The enzyme possesses proteolytic activity at pH values below 6 to above 11, with a pH optimum in the range of from pH 10 to pH 12; around pH 11.

The protease of the invention is stable for 60 minutes at 40° C. and under washing conditions, both with and without bleaches such as perborate and NOBS, in European and American type detergents.

Immunochemical Properties

The immunochemical properties can be determined immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

Monospecific antiserum was generated according to the above mentioned method by immunizing rabbits with the purified protease of the invention. The immunogen was mixed with Freund's adjuvant and injected subcutaneously into rabbits every second week. Antiserum was obtained after a total immunization period of 8 weeks, and immunoglobulin was prepared therefrom as described by N. H. Axelsen, supra.

Ouchterlony double immunodiffusion tests showed no cross reaction between the protease of the invention and the known alkaline serine proteases ALCALASE TM, SAVINASE TM, ESPERASE TM, Subtilisin BPN' and Protease API-21.

Detergent Compositions

The detergent composition of the invention may comprise one or more surfactants, which may be of an anionic, non-ionic, cat-ionic, amphoteric or zwitter-ionic type, or a mixture of these. Typical examples of anionic surfactants are linear alkyl benzene sulfonates (LAS); alkyl sulfates (AS); alpha olefin sulfonates (AOS); alcohol ethoxy sulfates (AES) and alkali metal salts of natural fatty acids. Examples of nonionic surfactants are alkyl polyethylene glycol ethers; nonylphenol polyethylene glycol ethers; fatty acids esters of sucrose and glucose; and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in J. Falbe [Falbe, J.; surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form, such as powders, liquids, etc.

The detergent composition of the invention may advantageously include one or more other enzymes, e.g. lipases; amylases; cellulases; and/or peroxidases, conventionally included in detergent compositions, as well as proteases of other origin.

The protease of the invention may be included in a detergent composition by adding separate additives containing the detergent protease, or by adding a combined additive comprising different detergent enzymes.

The additive of the invention, i.e. a separated additive or a combined additive, can be formulated e.g. as granulates, liquids, slurries, etc. Preferred detergent additive formulations are non-dusting granulates, liquids, in particular stabilized liquids, slurries, or protected enzymes. Dust free granulates may be produced according to e.g. GB Patent No. 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol; a sugar or sugar alcohol; lactic acid or boric acid, according to established methods. Other enzyme stabilizers are well known in the art. Protected enzymes may be prepared according to the method disclosed in EP Patent Application No. 238,216.

The following examples further illustrate the present invention.

EXAMPLE 1

Bacillus sp. J. 20 was cultivated at 25° C. on a rotary shaking table (300 r.p.m.) in 500 ml baffled Erlenmeyer flasks containing 100 ml of medium of the following composition (per liter):

| | |
|---|---|
| Potato starch | 100 g |
| Ground barley | 50 g |
| Soybean flour | 20 g |
| $Na_2HPO_4 \times 12 H_2O$ | 9 g |
| Pluronic ® | 0.1 g |
| Sodium caseinate | 10 g |

The starch in the medium is liquified with α-amylase and the medium is sterilized by heating at 120° C. for 45 minutes.

After sterilization the pH of the medium is adjusted to 9.7 by addition of 10 ml of a 1M solution of sodium sesquicarbonate.

After 5 days of incubation the proteolytic activity of the culture was determined using the method described above.

After cultivation, the enzyme activity of the broth was 120 CPU/l.

EXAMPLE 2

A pure enzyme preparation was prepared as follows: A fermented culture broth, prepared as described in Example 1, was centrifuged to remove solid material. To the centrifugate was added ½ volume of acetone, and the precipitate was removed by centrifugation and discarded. To the centrifugate was added further acetone to a total of 2 volumes. The precipitate was removed by centrifugation and dissolved in the following buffer: 0.1M boric acid; 0.01M dimethylglutaric acid; 0.002M calcium chloride; adjusted to pH 7.0.

From this solution the enzyme was isolated by affinity chromatography. The fractions with proteolytic activity were pooled, concentrated and washed with buffer in a ultra-filtration-cell and lyophilized.

Yield from 1 l of culture broth was 1.2 g with 25.6 CPU/g. Purity was more than 90% as judged by SDS-PAGE.

The characteristics of the enzyme preparation prepared in accordance with this Example have been referred to earlier in this specification, and reference is made hereto.

EXAMPLE 3

Wash Performance

The tests were performed at enzyme concentrations of 0.001; 0.01 and 0.10 CPU/l, the enzyme preparation being obtained according to Examples 1-2.

The wash performance tests were accomplished on mixed soiling (olive oil; gelatin; India ink; kaolin) on cotton, at 40° C., isothermally for 15 minutes.

1.5 g/l of a commercial American type liquid detergent were used. The detergent was dissolved in approx. 6° dH (German Hardness) water, and the pH was measured to 7.83. The textile/wash liquor ratio was 10 g of textile per liter of wash liquor. When the wash is over the pH has changed to 7.7.

Subsequent to washing, the cloths were flushed in running tap water and air-dried. The remission (% R) at 460 nm was determined.

As a measure of the wash performance differential remission, ΔR, was used being equal to the remission after wash with enzyme added, minus the remission after wash with no enzyme added.

The results of these tests are shown in Table 3.

TABLE 3

Wash performance of J20, an enzyme of the invention. The differential remission, Δ R, measured after wash in a commercial American type liquid detergent.

| Enzyme concentration CPU/l | ΔR |
| --- | --- |
| 0.001 | 3.1 |
| 0.01 | 10.3 |
| 0.10 | 16.1 |

The differential remission values show that the protease of the invention possesses excellent washability.

We claim:

1. An isolated protease having
   (a) an apparent molecular weight of 29 kD determined by SDS-PAGE;
   (b) a pI around 8.8;
   (c) a pH optimum above pH 10 at 25° C.;
   (d) a temperature optimum in the range of from 45° to 65° C. at pH 9.5; and
   (e) binds to a monospecific antibody raised against a protease derived from the strain Bacillus sp. J 20, NCIMB No. 40262.

2. An isolated protease according to claim 1, which is derived from a strain of the species Bacillus sp. J 20.

3. An isolated protease according to claim 2, which is derived from a strain Bacillus sp. J 20, NCIMB No 40262, or a mutant thereof which produces a protease having the same physical properties as the protease of claim 1.

4. A process for the preparation of a protease according to claim 1, which process comprises the steps of:
   (a) cultivating a protease producing strain of Bacillus sp. J 20 in a suitable nutrient medium, containing carbon and nitrogen sources and inorganic salts; and
   (b) recovering the enzyme.

5. A process according to claim 4, in which the protease producing strain is the strain Bacillus sp. J 20, NCIMB No. 40262, or a mutant thereof which produces a protease having the same physical properties as the protease of claim 1.

6. A detergent composition comprising an isolated protease according to claim 1, and a surfactant.

7. A detergent composition according to claim 6, further comprising one or more other enzymes selected from the group consisting of an amylase, a lipase, a cellulase and a peroxidase.

8. A detergent additive comprising an isolated protease according to claim 1, wherein said detergent additive is in the form selected from the group consisting of a non-dusting granulate, a liquid, a slurry and a protected enzyme.

9. The detergent additive according to claim 8, which is in the form of a stabilized liquid.

* * * * *